United States Patent [19]

Szepan

[11] Patent Number: 5,113,073
[45] Date of Patent: May 12, 1992

[54] METHOD AND APPARATUS FOR SPECTROSCOPIC QUANTITATIVE ANALYSIS OF GASES IN GAS MIXTURES

[76] Inventor: Reiner Szepan, Elecktrastrasse 26a, Munich D-8000, Fed. Rep. of Germany

[21] Appl. No.: 460,935
[22] PCT Filed: May 31, 1989
[86] PCT No.: PCT/EP89/00596
  § 371 Date: Mar. 20, 1990
  § 102(e) Date: Mar. 20, 1990
[87] PCT Pub. No.: WO89/12222
  PCT Pub. Date: Dec. 14, 1989

[30] Foreign Application Priority Data

Jun. 8, 1988 [DE] Fed. Rep. of Germany ....... 3819531

[51] Int. Cl.$^5$ ...................... G01N 21/59; G01J 3/433
[52] U.S. Cl. .................... 250/343; 250/373; 356/437
[58] Field of Search ............... 250/343, 344, 345, 373; 356/320, 435, 436, 437, 51

[56] References Cited

U.S. PATENT DOCUMENTS

| | | | |
|---|---|---|---|
| 4,027,972 | 6/1977 | Davies | 250/343 |
| 4,128,337 | 12/1978 | Zehnpfennig | 356/346 |
| 4,190,366 | 2/1980 | Doyle | 356/346 |
| 4,410,273 | 10/1983 | Mantz et al. | 356/51 |
| 4,441,815 | 4/1984 | Izunni | 250/373 |
| 4,641,973 | 2/1987 | Nestler et al. | 250/343 |
| 4,711,571 | 12/1987 | Schuman | 250/343 |

OTHER PUBLICATIONS

Olsowski et al., "Filter Correlation Photometer", Rev. of Sci. Instr., vol. 54, No. 6, (Jun. 1983) p. 722.
Force et al., "Laser Remote Sensing of Atmospheric Ammonia Using a $CO_2$ LIDAR", Applied Optics, vol. 24, No. 17 (Sep. 85) p. 2837.

Primary Examiner—Janice A. Howell
Assistant Examiner—Richard Hanig
Attorney, Agent, or Firm—Helfgott & Karas

[57] ABSTRACT

In a method of and an apparatus for spectroscopic quantitative analysis of gases in gas mixtures, periodically alternating monochromatic light of at least two wavelengths is used. The light of one wavelength is characteristic whereas light of the other wavelength is uncharacteristic of the transmission of the gas to be determined. The transmission generates electrical signals comprising harmonic components of at least one uneven Fourier frequency of an emission period, the amplitude of which is proportional to the concentration of the gas to be determined in the gas mixture, the Fourier frequency disappearing together with the concentration.

18 Claims, 5 Drawing Sheets

METHOD AND APPARATUS FOR SPECTROSCOPIC QUANTITATIVE ANALYSIS OF GASES IN GAS MIXTURES

BACKGROUND OF THE INVENTION

The invention relates to a method and apparatus for spectroscopic quantitative analysis of gases in gas mixtures.

The objects of the present invention are attained by a method of and apparatus for spectroscopic quantitative analysis of gases in gas mixtures with which monochromatic light of at least two wavelengths is used in periodically alternating fashion, the light of at least one wavelength being characteristic and the light of at least one other wavelength being uncharacteristic of the transmission of the gas to be determined, wherein the transmission generates electrical signals which comprise harmonic components of at least one uneven Fourier frequency of an emission period the amplitude of which is proportional to the concentration of the gas to be determined in the gas mixture and which vanishes together with the concentration.

The quantitative analysis of gases in gas mixtures is made on the basis of the absorption of radiation having a wavelength which is characteristic of the gas in question. Molecular gases dispose in particular of a pronounced characteristic for that purpose in the far infrared region.

Spectral distinction of the characteristic absorption by the gas to be analyzed from background radiation or from the uncharacteristic radiation damping along the transmission path is obtained by periodically sequencing the emission from a suitable source of radiation according to conventional analytical procedures at a wavelength which is characteristic of the particular gas and at a respective adjacent unspecific wavelength, with respective interruptions.

Lasers offer themselves as radiation sources; a dye laser is suitable for use in the visible region and a suitable molecular gas laser in the infrared region. The latter utilize the vibrational-rotational transitions of the respective gases. The molecular gas laser is set to the wavelengths of the respective desired emission lines by means of a resonator mirror or optical grating supported by a micropositioning means. The microposition can be controlled by electrical signals for generating the periodic emission sequence at different wavelengths.

In this context the quantitative analysis of ammonia in flue gases is of industrial-scale importance. Flue gases are produced with every atmospheric combustion and together with them necessarily also nitrogen oxides $NO_x$. The latter, on the one hand, can be reduced to products which are free of noxious components by feed ammonia. On the other hand, the so-called "slip", in other words a noticeable excess of ammonia is undesired.

By law of nature one line each of the vibration-rotation bands of ammonia and $^{13}C^{16}O_2$ coincide at wavelength 9.89 μm within the line widths at normal or operating conditions of a furnace. Therefore, the absorption of the radiation of a tuned $^{13}C^{16}O_2$ laser in a gas mixture informs about the content of ammonia.

If the gas to be analyzed—in the instant case ammonia in flue gas—is present in traces, the specific and unspecific absorptions in the laser emission sequence differ only little so that the transmission signals of the sequence are only little different from one another and, in addition, contain incoherent signal noise contributions from the laser emission, the noise in the measuring section and in the detector means. These circumstances make it necessary to apply long signal integration times in order to obtain the signal reliability as required, for instance, in industrial applications. That, on the other hand, means that the arrangement must meet high operational stability requirements.

SUMMARY OF THE INVENTION

It is the object of the invention to develop a method and an apparatus of the generic kind in question such that a certain porportion of gas in a gas mixture can be determined better.

The objects of the present invention are attained by a method of an apparatus for spectroscopic quantitative analysis of gases in gas mixtures with which monochromatic light of at least two wavelengths is used in periodically alternating fashion, the light of at least one wavelength being characteristic and the light of at least one other wavelength being uncharacteristic of the transmission of the gas to be determined, wherein the transmission generates electrical signals which comprise harmonic components of at least one uneven Fourier frequency of an emission period the amplitude of which is proportional to the concentration of the gas to be determined in the gas mixture and which vanishes together with the concentration.

In an advantageous embodiment of the method according to the invention the harmonic signal components of at least one uneven Fourier frequency and those of an even Fourier frequency are related to each other and the relationship thus established is a measure of the characteristic absorption.

With another advantageous embodiment of the method according to the invention the second Fourier component of the electrical signal becomes the maximum.

With another advantageous embodiment of the method according to the invention the emission of the radiation pulses used is effected each at constant energy, and the pulse center spacing corresponds to half the emission period.

With another advantageous embodiment of the method according to the invention the emissions of both transmissions producing the different wavelengths are of the same duration and are separated by phases of the same duration which are free of emissions.

In the case of another advantageous embodiment of the method according to the invention the respective emission phases and the emission-free phases are of equal duration.

With an advantageous embodiment of the apparatus according to the invention the gas is ammonia and the light source is a laser, especially a $^{13}C^{16}O_2$ laser which emits periodically alternating radiation of the quantum mechanical P8II transition of the vibration-rotation spectrum and of an adjacent transition (e.g. P6II or P10II).

Another advantages embodiment of the apparatus according to the invention comprises a circuit means for adapting the electrical signals to one another.

In the case of another advantageous modification of the apparatus according to the invention the duration of emission of the higher energy of laser 1 is decreased or increased, centered about the middle.

Another advantageous embodiment of the apparatus according to the invention includes an infrared detector comprising signal amplitudes which originate from the wavelength sequenced laser emission and from the transmission of a gas containing ammonia, respectively. And a symmetry mixing circuit is provided which is linked with a signal of the second Fourier frequency of the emission period.

With another advantageous embodiment of the apparatus according to the invention the above mentioned mixed products, having been filtered in a device, are subjected to synchronous rectification which is controlled by a signal of the first Fourier frequency of the emission period.

Another advantageous modification of the apparatus according to the invention comprise a quotient circuit by means of the signal ratios of which a magnitude which is independent of the emission intensity of the light source and of the non-spectral transmission reductions is produced from the filtered rectifier products and from the equal share of the mixed product.

With another advantageous modification of the apparatus according to the invention the signal amplitudes of an infrared detector originating from the wavelength sequenced emission of the light source are applied, as the error signal, to a porportional control loop which adjusts the sequential amplification of the signal of the infrared detector or the duration of emission.

In the case of another advantageous embodiment of the apparatus according to the invention an optical resonator of the laser is modulated periodically as to wavelength, and the resulting modulation frequency signal components of an infrared detector, as a consequence of the laser emission variation, serve as error magnitude in an integral control loop to maximize the respective emissions.

Another advantageous modification of the apparatus according to the invention comprises a reference cuvette through which the wavelength sequenced emission of the laser radiates, an operational characteristic magnitude being produced which is proportional to the reference gas quantity.

BRIEF DESCRIPTION OF THE DRAWINGS

The invention will be described further, by way of example, with reference to the accompanying drawings, in which.

DETAILED DESCRIPTION OF THE PREFERRED EMBODIMENT

Figure 1:
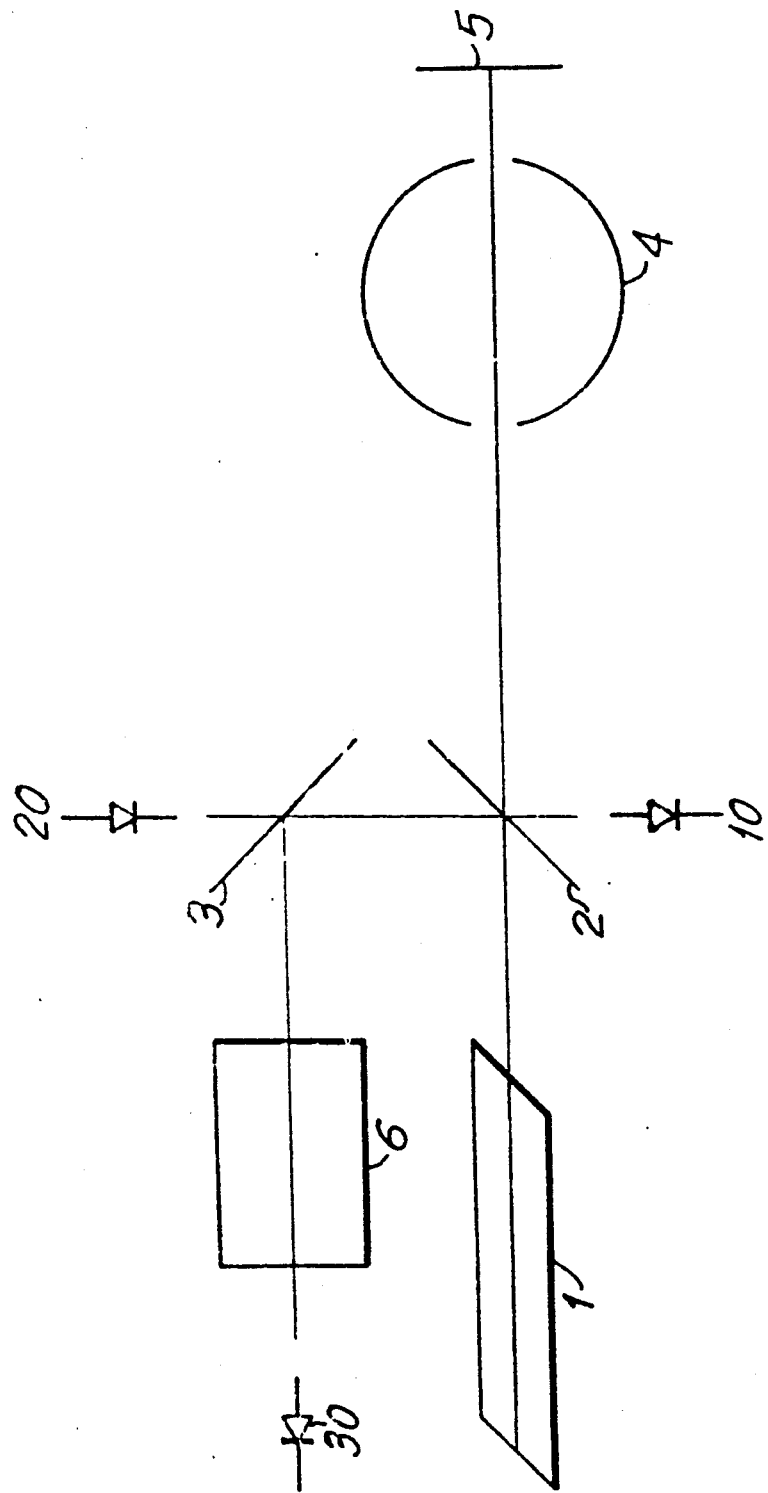
FIG. 1 is a diagrammatic presentation of the optical arrangement according to the invention.
Figure 5:
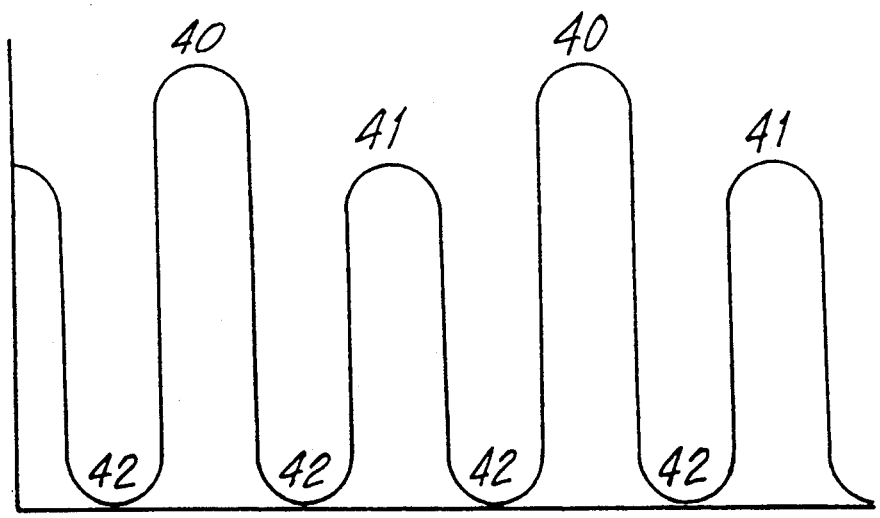
FIG. 5, 5a, 5b show electronic signal patterns.
Figure 5A:
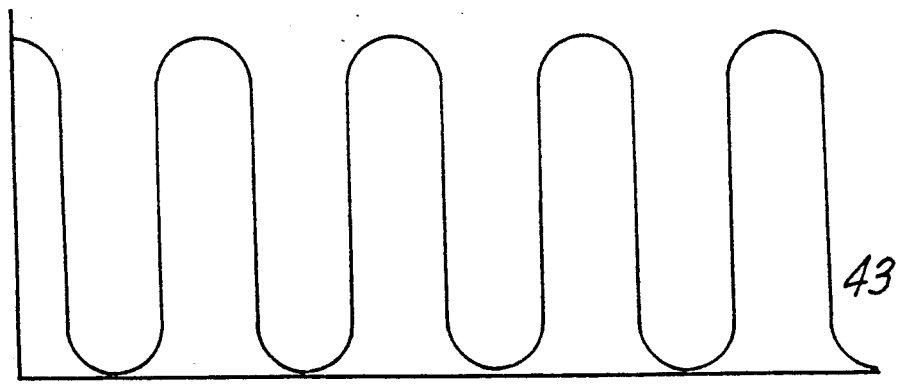
Figure 5B:
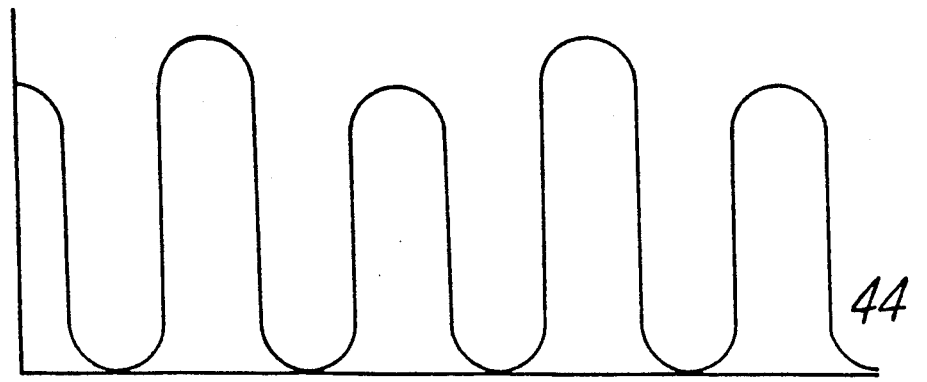

FIG. 1 shows a laser 1 radiating a gas 4 to be analyzed through an analysis space. The laser generates a periodic sequence of two emissions 40,41 separated by pauses or at least by attenuation phases 42 and each having a respective associated wavelength, as illustrated in FIG. 5. This period is referred to below as the emission period and the reciprocal value of integer partial ratios of the emission-period is designated Fourier frequency of the order corresponding to the parial ratio.

It is advantageous to determine the quantity of ammonia gas, for instance, in flue gases by the emission of the quantum mechanical transition P8II of the vibration-rotation spectrum of a $^{13}C^{16}O_2$ laser, as the characteristic proof, because of the selective properties and the efficiency thereof.

The narrow-band coherent signal process methods of the instant invention are used in addition to the dominant emission level of the laser 1 and the noise signal super-positioning for the technical signal process domination of the variation in transmission which is differentially small and appears because of the absorption of the gas 4 to be analyzed in an optical measuring section (beam splitter 2, analysis space containing gas 4, retroreflector 5, radiation detector 10). Accordingly, an alternating electrical signal is generated which has the frequency of an uneven Fourier component of the emission period, the amplitude thereof being proportional to the laser emission energy and the transmission losses, resulting from the characteristic absorption, and disappearing with the characteristic transmission losses. Moreover, an electrical signal is generated which has the frequency of an even Fourier component of the emission period, the amplitude thereof being proportional to the energy of at least one emission pulse. That requires conditioning of the emission or of the electrical signals which are obtained by suitable radiation detectors 10,20,30 including amplifiers, as the receivers of the emission.

Figure 3:
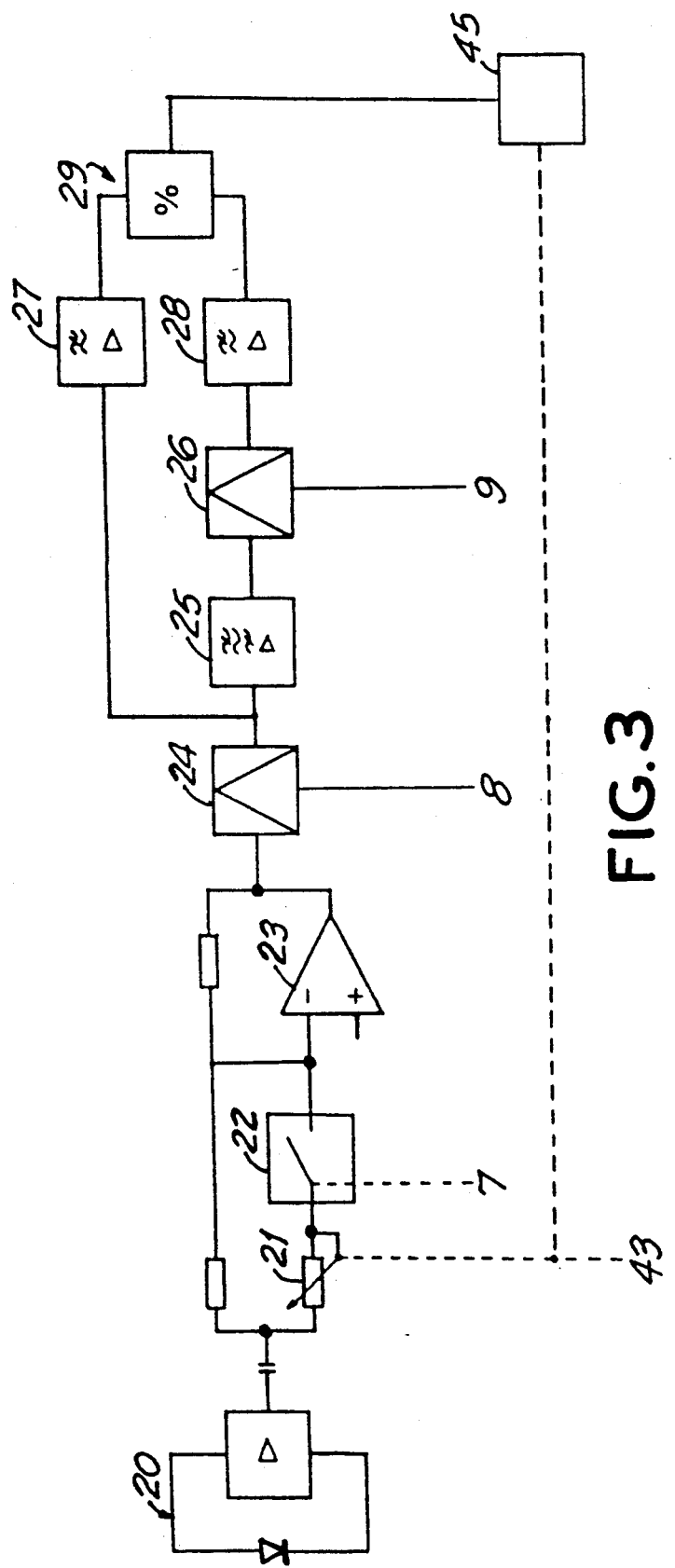
FIG. 3 is a diagrammatic circuit arrangement for signal conditioning.
Figure 4:
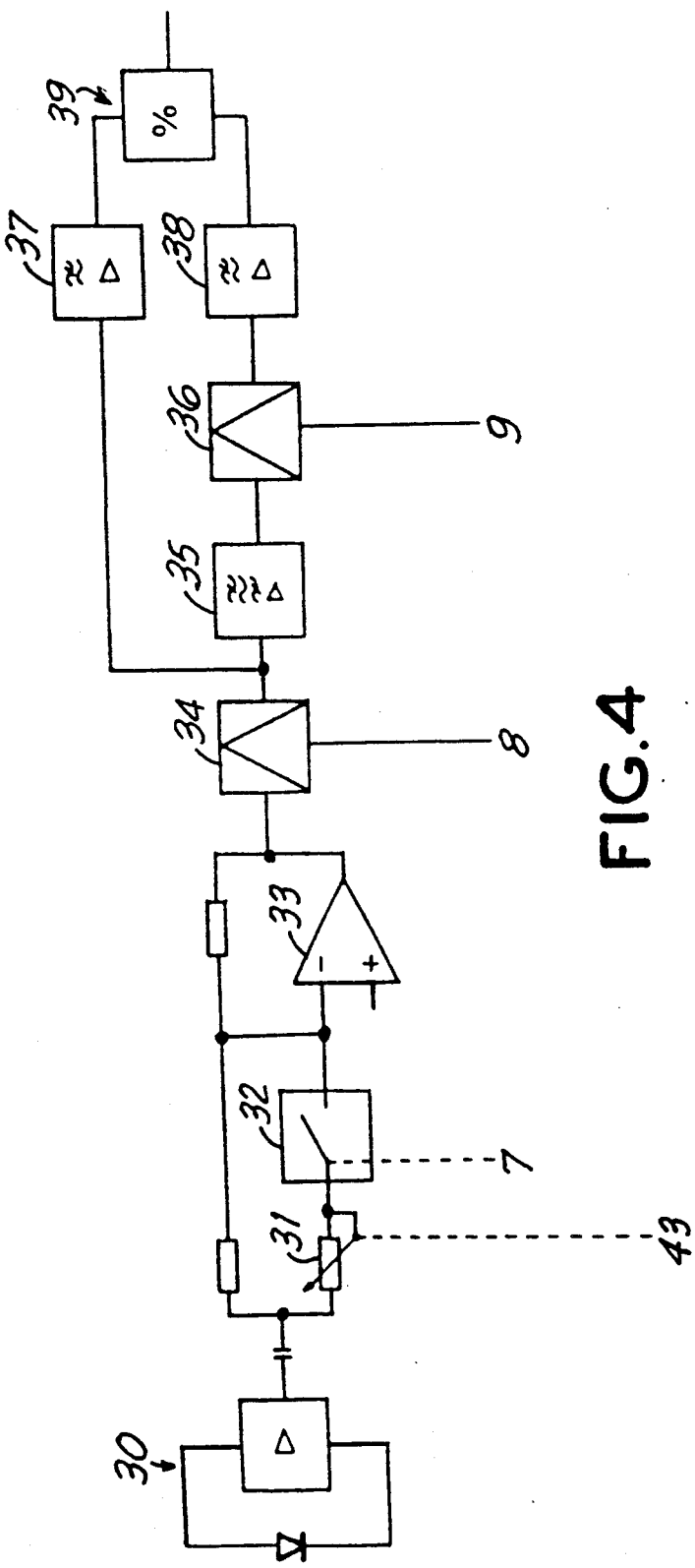
FIG. 4 is a diagrammatic circuit arrangement for gauging.

This signal conditioning is accomplished in two ways by control arrangements such as shown in FIG. 3, for example, resorting to a separate optical section 2,20 which contains no shares of the gas 4 to be found and to a separate electrical signal section 20 . . . 29.

As shown in FIG. 5, the centers of two radiation pulses 40,41 of constant energy each are spaced by half the emission period. The radiation pulse 40 of higher energy is extended or shortened, centered about the middle, such that the first Fourier component of the emission period disappears at the detector 30. Component parts 11,12,13, 21,22,23 31,32,33 which will be explained in greater detail below do not apply here.

The spacing between centers of the two radiation pulses 40,41 of constant energy each corresponds to half the emission period. A summing amplifier 23 takes care of an adaptive rise of the gain of the weaker pulse 41 at the detector 20 and of an adaptive attenuation of the stronger pulse by switching on (22) or off an electronic potentiometer 21 in the associated emission phase 7 so that the first Fourier component 44 and 43, respectively, of the emission period will disappear at the output of the amplifier 23.

The conditioned signal mixture at the input of the symmetry mixing circuit 24 is mixed in the same with a signal 8 of the second Fourier frequency of the emission period. The signal components of this particular frequency disappear or are attenuated so that all that is available beyond the filter circuit and an optional amplifier circuit 25 is signal components of the first Fourier frequency of the emission period which components originate from detuning of the signal conditioning according to FIG. 3. The magnitude and sign of such signal components are given by the output signal 28 of the synchronous rectifier 26 which is switched by a signal of the first Fourier frequency 9 of the emission period. The rectifier signals 24, 26 are smoothed in low pass filter circuits 27,28, the sum group delay time of the filters 25,28 corresponding to the group delay time of the filter 27. A quotient circuit 29 supplies a control error which is independent of the radiation intensity and influences the adjusting members (micropositioning or potentiometer 43) by way of a control circuit 45 such that the first Fourier component disappears at the mixer input 24.

Figure 2:
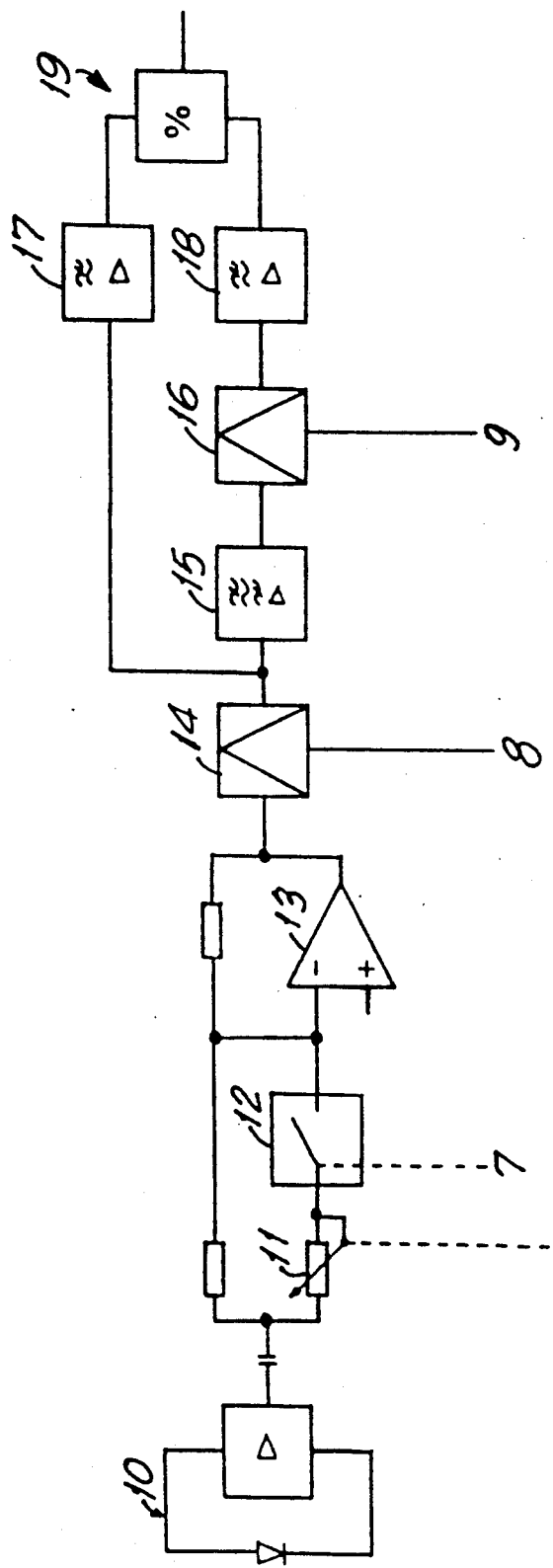
FIG. 2 is a diagrammatic circuit arrangement for the quantitative gas analysis.

The gas-characteristic attenuation of transmission along the measuring section 2,4,5,10 is a measure of the concentration of the gas 4 to be analyzed In accordance with the invention this magnitude is represented, after the signal conditioning 20 . . . 29,45, as an electrical signal of an uneven—preferably the first—Fourier frequency of the emission period. The structure of the measuring signal section 10 . . . 19 shown in FIG. 2 corresponds identically to that of the conditioning section 20 . . . 29.

The radiation detector 10 measures the wavelength specific transmission of the gas 4 to be examined and amplifies it, if desired. As the emission energies of the pulses 40,41 differ, at the wavelengths applied, a pulse width correction is effected by the conditioning, or the summing amplifier 13 carries out an adaptive raising of the amplification of the weaker emission signal or an adaptative weakening of the stronger emission signal by switching on 12 or off an electronic potentiometer 11 in the associated emission phase 7 which potentiometer is synchronized with potentiometer 21.

The existence of signal components of the first Fourier frequency in the mixed products 15 is due solely to the specific radiation absorption of the gas 4 to be analyzed once the conditioning 20...29,45 has been completed. Their magnitude is proportional to the concentration of the gas 4 to be analyzed. In applying this coherent analytical procedure it becomes possible by the invention to isolate a very weak signal specific of a gas, apart from the dominant emission signal. The signal of the first Fourier frequency of the emission period is separated by a filter 15 from the mixed products and amplified, if desired. Finally, the gas-specific useful signal is applied to the synchronous rectifier 16 which is switched by the first Fourier frequency and which thus reflects the intensity of the useful signal characteristic of the gas. The quotient 19 of the filtered signals 17,18 represents a process magnitude which is independent of the intensity, proportional to the concentration of the gas 4 to be analyzed and also highly resolved, thanks to the coherent signal processing technique. The contributions from incoherent signal noise components are reduced by this method and apparatus for the selective spectroscopic quantitative analysis of gases in gas mixtures so that rapid, reliable data sequences 19 are available which are needed for industrial application.

A problem of apparatus stability crops up when using lasers 1 as the source of radiation involving the centering of the optical resonator or filter to the respective emission maxima. The micropositioning means carrying the resonator or filter and being driven electrically carries out swinging motion which causes the alternating emission of radiation of at least two wavelengths. A periodic small slower motion is superposed over that swinging motion. The spectral signal component of the frequency of this scanning motion in the error signal 29 of the proportional control circuit 45 for conditioning, furthermore, represents an error signal of the integral control for micropositioning to obtain the maximum emission.

Another problem of apparatus stability is involved in the start-up of the process and apparatus for the selective spectroscopic quantitative analysis of gases 4 in gas mixtures. This problem is solved in accordance with the invention by a reference section 1,2,3,6,30. This solution of the problem is of the greatest significance when setting into operation redundant systems with operational tasks.

A beam splitter 3 couples a part out of the laser radiation emitted and this part impinges on the beam detector 30 after having passed through a cuvette 6 which contains the gas to be analyzed. The signal processing 30 . . . 39 corresponds to that of the useful signal section 10 . . . 19 or conditioning section 20 . . . 29. The circuit arrangement generates a signal 39 which is coordinated within given tolerance limits with a calibration quantity in the cuvette 6.

The maladjustment of the laser arrangement essentially is due to the aging of component parts and to thermal influences. Upon switch-on a search run is started which may be processor controlled, if desired, and which searches the range of the wavelength-harmonizing micropositioning means of the laser for the reference condition in the reference section 3,6,30 and effects the operational positioning.

The arrangement 2 . . . 45 may be designed such that the emission of another laser is coupled into the arrangement if the operational laser 1 should fail.

The determination of the absolute quantity of the ammonia contained in the gas 4 to be analyzed is calculated in a signal process computer based on the process measuring data 29, the emission width of the laser 1, the absorption width of the ammonia vapor, and the line shift of the laser emission and the ammonia absorption.

What is claimed is:

1. A method of spectroscopic quantitative analysis of gases in gas mixtures with which monochromatic light of at least two wavelengths is used in periodically alternating fashion, the light of at least one wavelength being characteristic and the light of at least one other wavelength being uncharacteristic of the transmission of the gas to be determined, wherein this transmission generates electrical signals which comprise harmonic components of at least one uneven Fourier frequency of an emission period the amplitude of which is proportional to the concentration of the gas to be determined in the gas mixture and which vanishes together with the concentration.

2. The method as claimed in claim 1, wherein a ratio is established between the harmonic signal components of at least one uneven Fourier frequency and those of an even Fourier frequency, and that this ratio is a measure of the characteristic absorption.

3. The method as claimed in claim 1, wherein the second Fourier component of the electrical signal becomes the maximum.

4. The method as claimed in claim 1, wherein emission of radiation pulses used is effected at respective constant energy and pulse centers are spaced by half the emission period.

5. The method as claimed in claim 1, wherein emissions of both transitions which produce the different wavelengths are of the same duration each and are separated by emission-free phases of equal duration each.

6. The method as claimed in claim 5, wherein respective emission phases and the emission-free phases are of equal duration.

7. An apparatus for spectroscopic quantitative analysis of gases in gas mixture, comprising a monochromatic light source which emits periodically alternating light of at least two wavelengths, the light of at least one wavelength being characteristic and the light of at least one other wavelength being uncharacteristic of the transmission of the gas to e determined; and a mauling section (2,4,5,10) which contains the gas to be measure and an optical reference section (20 . . . 29) without characteristic gas absorption for generating, during said transmission, electrical signals including harmonic components of at least one uneven Fourier frequency of an emission period the amplitude of which is proportional to the concentration of the gas to be determined in the gas mixture so as to determine electrical signals which are proportional to the concentration of the gas in the measuring section (2,4,5,10).

8. The apparatus as claimed in claim 7, wherein the gas is ammonia and the light source (1) is a $^{13}C^{16}O_2$ laser which periodically alternatingly emits radiation of the quantum mechanical P8II transition of the vibration-rotation spectrum and of an adjacent transition.

9. The apparatus as claimed in claim 7, wherein a circuit means (20-29) is provided by which the electrical signals are adapted to one another.

10. The apparatus as claimed in claim 8, wherein the duration of emission of the higher energy of the laser (1) is decreased, centered about the middle.

11. The apparatus as claimed in claim 8, wherein an infrared detector (10, 20, 30) is provided comprising signal amplitudes which result from the wavelength sequenced laser emission or the transmission of a gas containing ammonia, and wherein a symmetry mixing circuit (15, 25, 30) is provided which is linked with a signal of the second Fourier frequency of the emission period (8).

12. The apparatus as claimed in claim 8, further comprising a filter device (51, 25, 35) and a synchronous rectifier (16, 26, 36), wherein mixed products (14, 24, 34) are filtered in the filter device (15, 25, 35) and are subjected to synchronous rectification in said rectifier (16, 26, 36), said rectifier being controlled by a signal of the first Fourier frequency of the emission period (9).

13. The apparatus as claimed in claim 12, further comprising a quotient circuit (19, 29, 30), by means of the signal ratios (53, 62) of which a magnitude, which is independent of the emission intensity of the light source (1) and of the non-spectral transmission reductions, is produced from filtered rectifier products (18, 28) and from the equal share of the mixed product (17, 27, 37).

14. The apparatus as claimed in claim 7, further comprising an infrared detector (20) for supplying the signal amplitudes resulting from the wavelength sequenced emission of the light source (1), as an error signal, to a proportional control loop which adjusts a sequential amplification of the signal from the infrared detector (20).

15. The apparatus as claimed in claim 8, wherein an optical resonator of the laser (1) is modulated periodically as a wavelength, and further comprising an infrared detector (10, 20, 30), wherein the resulting modulation frequency signal components of the infrared detector (10, 20, 30) due to the laser emission variation serve as an error magnitude in an integral control loop to maximize the respective emissions.

16. The apparatus as claimed in claim 8, wherein a reference cuvette (6) is provided through which the wavelength sequenced emission of the laser (1) radiates to produce an operational characteristic magnitude which is proportional to the reference gas quantity.

17. The apparatus as claimed in claim 8, wherein a circuit means (20-29) is provided by which the electrical signals are adapted to one another.

18. The apparatus as claimed in claim 9, wherein the duration of emission of the higher energy of the laser (1) is increased, center about the middle.

* * * * *